(12) United States Patent
Jung et al.

(10) Patent No.: US 9,095,879 B2
(45) Date of Patent: Aug. 4, 2015

(54) PROBE FOR ULTRASONIC DIAGNOSTIC APPARATUS AND METHOD OF MANUFACTURING THE SAME

(75) Inventors: Jin Woo Jung, Seoul (KR); Jeong Cheol Seo, Gwangju-si (KR); Jae Yk Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 328 days.

(21) Appl. No.: 12/725,371

(22) Filed: Mar. 16, 2010

(65) Prior Publication Data

US 2010/0241004 A1 Sep. 23, 2010

(30) Foreign Application Priority Data

Mar. 18, 2009 (KR) ........................ 10-2009-0023014

(51) Int. Cl.
*A61B 8/14* (2006.01)
*B06B 1/06* (2006.01)
*G10K 11/00* (2006.01)

(52) U.S. Cl.
CPC ............ *B06B 1/0622* (2013.01); *G10K 11/004* (2013.01); *Y10T 29/49005* (2015.01)

(58) Field of Classification Search
USPC ......................................... 600/407, 437–475
See application file for complete search history.

(56) References Cited

U.S. PATENT DOCUMENTS 5,637,800 A * 6/1997 Finsterwald et al. ............ 73/642
6,308,389 B1 * 10/2001 Tezuka ......................... 29/25.35
2008/0015443 A1 1/2008 Hosono et al.

FOREIGN PATENT DOCUMENTS

| EP | 2 025 414 A1 | 2/2009 |
|---|---|---|
| JP | 08-280095 A | 10/1996 |
| JP | 10229597 A | 8/1998 |
| JP | 2000-166923 A | 6/2000 |
| JP | 2004-514340 A | 5/2004 |
| JP | 2006-095178 A | 4/2006 |

OTHER PUBLICATIONS

European Search Report issued in European Patent Application No. 10152553.3 dated Jul. 20, 2010.
Japanese Office Action issued in Application No. 2010-058060 dated Apr. 8, 2014.

* cited by examiner

*Primary Examiner* — Mark Remaly
(74) *Attorney, Agent, or Firm* — McDermott Will & Emery LLP

(57) ABSTRACT

A probe for an ultrasonic diagnostic apparatus includes including backing members, a first connector bonded between the backing members and including electrodes spaced from each other in an arrangement direction, a ground connector bonded between the backing members to be spaced from the first connector, and a piezoelectric member electrically connected to the electrodes and the ground connector. A method of manufacturing the same is also disclosed. The piezoelectric member is joined to the first connector and the ground connector or to first and second connectors and the ground connector via first and second electrode layers instead of using a complicated and laborious soldering operation, thereby enabling easy connection between the piezoelectric member and the connectors while preventing deterioration in performance caused by defective connection therebetween and deterioration in performance of the piezoelectric member caused by heat during manufacture.

14 Claims, 17 Drawing Sheets

PROBE FOR ULTRASONIC DIAGNOSTIC APPARATUS AND METHOD OF MANUFACTURING THE SAME

CROSS-REFERENCE TO RELATED APPLICATIONS

The present application claims priority from Korean Patent Application No. 10-2009-0023014 filed on Mar. 18, 2009, the entire subject matter of which is incorporated herein by reference.

BACKGROUND OF THE INVENTION

1. Field of the Invention

The present invention relates to probes and, more particularly, to a probe for an ultrasonic diagnostic apparatus that generates internal images of a patient body using ultrasound waves, and a method of manufacturing the same.

2. Description of the Related Art

Generally, an ultrasonic diagnostic apparatus refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasonic diagnostic apparatus has been widely used for diagnosis of the heart, the abdomen, the urinary organs, and in obstetrics and gynecology due to various merits such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

The ultrasonic diagnostic apparatus includes a probe which transmits an ultrasound signal to a patient body and receives the ultrasound echo-signal reflected therefrom to obtain the ultrasound image of the patient body.

The probe includes a transducer, a case with an open upper end, a cover coupled to the open upper end of the case to directly contact the body surface of the patient, and the like.

The transducer includes a piezoelectric layer in which a piezoelectric material converts electrical signals into sound signals or vice versa while vibrating, a sound matching layer reducing a difference in sound impedance between the piezoelectric layer and a patient body to allow as much of the ultrasound waves generated from the piezoelectric layer as possible to be transferred to the patient body, a lens layer focusing the ultrasound waves, which travel in front of the piezoelectric layer, onto a predetermined point, and a backing layer blocking the ultrasound waves from traveling in a rearward direction of the piezoelectric layer to prevent image distortion.

The piezoelectric layer includes a piezoelectric member and electrodes provided to upper and lower ends of the piezoelectric member, respectively. Further, a printed circuit board (PCB) is bonded to the piezoelectric layer. The PCB is provided with wiring electrodes that are connected to the electrodes of the piezoelectric layer to transfer signals from the piezoelectric member. The PCB is connected to the piezoelectric layer by connecting the wiring electrodes of the PCB and the electrodes of the piezoelectric layer.

In fabrication of the probe, connection of the wiring electrodes of the PCB to the electrodes of the piezoelectric layer is a laborious operation, which increases fabrication time and causes deterioration in performance of the probe due to low durability and non-uniformity of a connected part therebetween. Therefore, there is a need to provide a probe for an ultrasonic diagnostic apparatus that overcomes such problems.

SUMMARY OF THE INVENTION

The present invention is conceived to solve the problems of the related art as described above, and an aspect of the present invention is to provide an improved probe for an ultrasonic diagnostic apparatus configured to allow easy manufacture of the probe while preventing deterioration in performance caused by defective connection between a piezoelectric layer and a PCB, and a method of manufacturing the same.

In accordance with one aspect of the invention, a probe for an ultrasonic diagnostic apparatus includes: a backing layer including backing members; a first connector bonded between the backing members and including electrodes spaced from each other in an arrangement direction; a ground connector bonded between the backing members to be spaced from the first connector; and a piezoelectric member electrically connected to the electrodes and the ground connector.

At least one of the first connector and the ground connector may include a flexible printed circuit board (FPCB).

The backing layer may include a first electrode layer electrically connected to the electrodes.

The first electrode layer may be formed on a surface of the backing layer.

The backing layer may further include a second electrode layer electrically connected to the ground connector.

The second electrode layer may be formed on the surface of the backing layer to be separated from the first electrode layer.

The backing layer may be formed with a mounting groove, and the piezoelectric member may be inserted into the mounting groove.

The probe may further include a second connector bonded between the backing members and including electrodes spaced from each other in the arrangement direction.

The second connector may be disposed in the height direction of the backing members such that the electrodes of the first connector alternate with the electrodes of the second connector.

The electrodes of the first and second connectors may be signal electrodes.

In accordance with another aspect of the invention, a method of manufacturing a probe for an ultrasonic diagnostic apparatus includes: forming electrodes on a first connector to be spaced from each other in an arrangement direction; forming a ground connector; forming a backing layer by bonding the first connector and the ground connector between backing members; and stacking a piezoelectric member on the backing layer to be electrically connected to the electrodes and the ground connector.

The method may further include forming a first electrode layer on the backing layer to be electrically connected to the piezoelectric member and the electrodes after forming the backing layer.

The method may further include forming a second electrode layer on the backing layer to be electrically connected to the piezoelectric member and the ground connector after forming the backing layer.

The forming a second electrode layer on the backing layer may include forming the second electrode layer to be separated from the first electrode layer.

In accordance with a further aspect of the invention, a method of manufacturing a probe for an ultrasonic diagnostic apparatus includes: forming electrodes on a first connector to be spaced from each other in an arrangement direction; forming electrodes on a second connector to be spaced from each other in the arrangement direction; forming a ground connector; forming a backing layer by bonding the ground connector, the first connector and the second connector between backing members; and stacking a piezoelectric member on the backing layer to be electrically connected to the ground connector and the electrodes of the first and second connectors.

The method may further include forming a first electrode layer on the backing layer to be electrically connected to the piezoelectric member, the ground connector, and the electrodes of the first and second connectors after forming the backing layer.

The forming a backing layer may include disposing the second connector in a height direction of the backing members such that the electrodes of the first connector alternate with the electrodes of the second connector.

The method may further include forming a second electrode layer on the backing layer to be electrically connected to the piezoelectric member and the ground connector after forming the backing layer.

The forming a second electrode layer on the backing layer may include forming the second electrode layer to be separated from the first electrode layer.

The method may further include forming a mounting groove on the backing layer, wherein the stacking a piezoelectric member on the backing layer includes inserting the piezoelectric member into the mounting groove.

BRIEF DESCRIPTION OF THE DRAWINGS

The above and other aspects, features and advantages of the invention will become apparent from the following description of embodiments given in conjunction with the accompanying drawings, in which.

DETAILED DESCRIPTION OF THE EMBODIMENT

Exemplary embodiments of the invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the invention into account and can be changed according to the custom or intention of users or operators. Therefore, definition of the terms should be made according to overall disclosures set forth herein.

Figure 1:
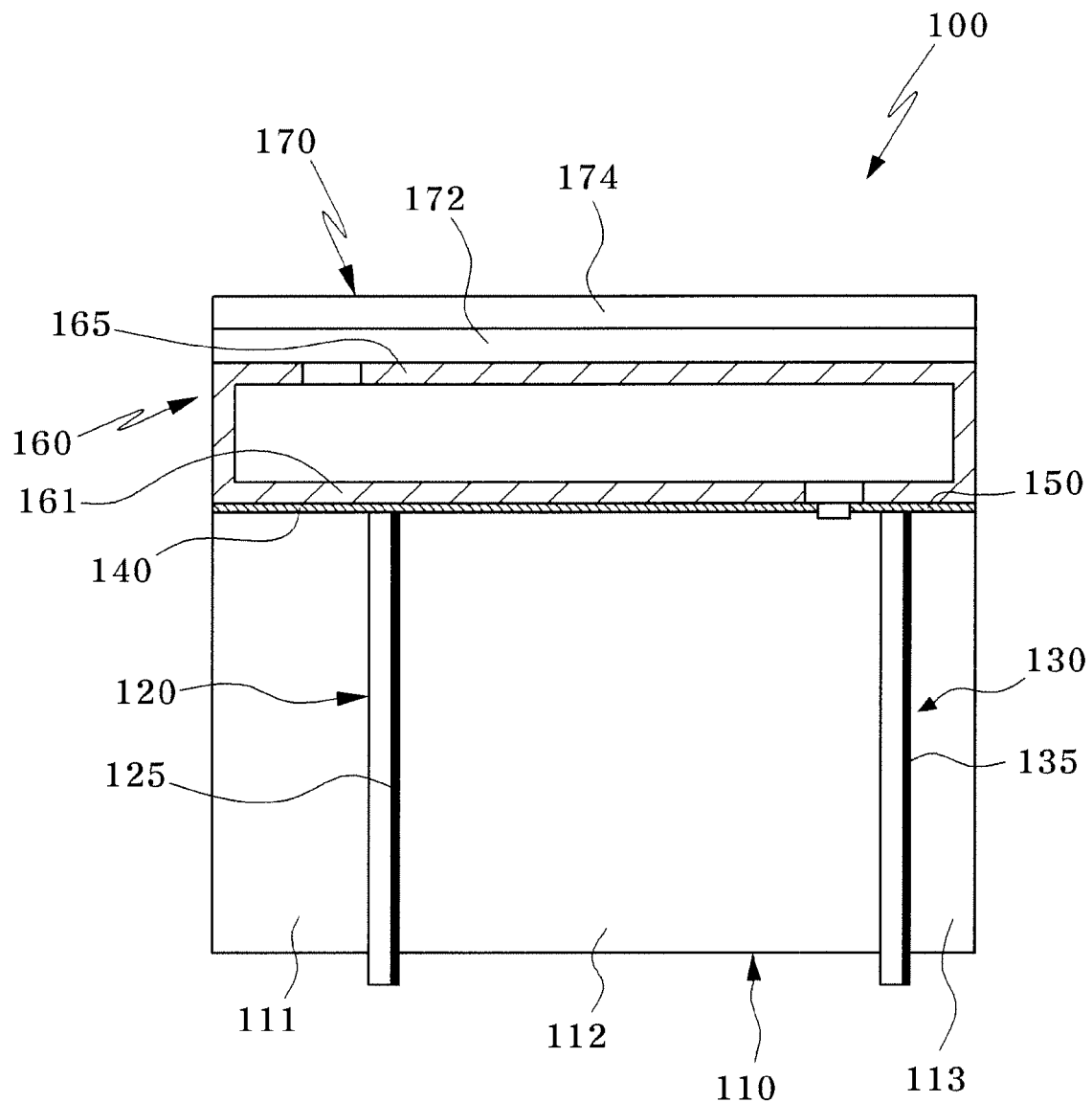
FIG. 1 is a schematic view of a probe for an ultrasonic diagnostic apparatus according to a first embodiment of the present invention.

FIG. 1 is a schematic view of a probe for an ultrasonic diagnostic apparatus according to a first embodiment of the invention.

Referring to FIG. 1, a probe 100 for an ultrasonic diagnostic apparatus according to this embodiment includes a backing layer 110, a first connector 120, a ground connector 130, and a piezoelectric member 160.

The backing layer 110 is disposed behind the piezoelectric member 160 described below. The backing layer 110 reduces a pulse width of an ultrasound wave by suppressing free vibration of the piezoelectric member 160 and prevents image distortion by blocking unnecessary propagation of the ultrasound wave in the rearward direction of the piezoelectric member 160.

The backing layer 110 includes multiple backing members 111, 112, 113 and is formed by bonding the backing members 111, 112, 113. The backing layer 110 may be formed of a material containing a rubber to which epoxy, tungsten powder, and the like are added.

The first connector 120 includes an insulation part (reference numeral omitted) and electrodes 125. The multiple electrodes 125 are disposed on the insulation part to be separated from each other in an "arrangement direction." Herein, the term "arrangement direction" refers to a direction in which multiple piezoelectric members 160 are arranged in an array. In other words, the electrodes 125 are spaced from each other in the arrangement direction of piezoelectric members 160 arranged in an array (see FIG. 3).

In this embodiment, each of the electrodes 125 of the first connector 120 is a signal electrode that is electrically connected to a first electrode 161 of the piezoelectric member 160 described below.

The first connector 120 including the electrodes 125 is bonded between the backing members 111, 112, 113. According to this embodiment, the first connector 120 is inserted and bonded between two backing members 111, 112 among the three backing members 111, 112, 113.

The first connector 120 is disposed in a "height direction of the backing members 111, 112, 113." The backing members 111, 112 are bonded to opposite sides of the first connector 120, thereby forming a part of the backing layer 110. Herein, the term "height direction of the backing members 111, 112, 113" refers to a direction perpendicular to a direction in which a first electrode layer 140 described below is formed (see FIG. 3).

One end of the first connector 120 bonded between the backing members 111, 112 is exposed on a front side of the backing layer 110 adjacent to the piezoelectric member 160, and the other end thereof extends through a rear side of the backing layer 110. As such, since the one end of the first connector 120 is exposed on the front side of the backing layer 110, the electrodes 125 of the first connector 120 are exposed on the front side of the backing layer 110.

The first connector 120 may include a flexible printed circuit board (FPCB), a printed circuit board (PCB) or any configuration capable of supplying signals or electricity.

The ground connector 130 is bonded between the backing members 112, 113. According to this embodiment, the ground connector 130 is inserted and bonded between the two backing members 112, 113 among the three backing members 111, 112, 113. The ground connector 130 is spaced from the first connector 120 by a width occupied by the backing member 112.

The ground connector 130 includes an insulation part (reference numeral omitted) and multiple electrodes 135. Like the electrodes 125 of the first connector 120, the multiple electrodes 135 are spaced from each other in the arrangement direction. Alternatively, the electrodes 135 may be formed to constitute the entirety of the ground connector 130.

In this embodiment, the multiple electrodes 135 are formed on the ground connector 130 and are ground electrodes, each of which is electrically connected to the second electrode 165 of the piezoelectric member 160 described below.

The ground connector 130 including the electrodes 135 is disposed in the height direction of the backing members 111, 112, 113. The backing members 112, 113 are bonded to opposite sides of the ground connector 130, thereby forming the backing layer 110 along with the backing member 111.

One end of the ground connector 130 bonded between the backing members 112, 113 is exposed on the front side of the backing layer 110 adjacent to the piezoelectric member 160, and the other end thereof extends through the rear side of the backing layer 110. As such, since the one end of the ground connector 130 is exposed on the front side of the backing layer 110, the electrodes 135 of the ground connector 130 are exposed on the front side of the backing layer 110.

The backing layer 110 includes the first electrode layer 140. The first electrode layer 140 is formed on the backing layer 110 to be disposed between the backing layer 110 and the piezoelectric member 160. The first electrode layer 140 is electrically connected to the electrodes 125 of the first connector 120.

According to this embodiment, the first electrode layer 140 is formed on a surface of the backing layer 110. Specifically, the first electrode layer 140 may be formed on the front surface of the backing layer 110 adjacent to the piezoelectric member 160.

The backing layer 110 may further includes a second electrode layer 150. The second electrode layer 150 is also formed on the backing layer 110 to be disposed between the backing layer 110 and the piezoelectric member 160. The second electrode layer 150 is electrically connected to the electrodes 135 of the ground connector 130.

The second electrode layer 150 may be formed on the surface of the backing layer 110, particularly, on the front surface of the backing layer 110 adjacent to the piezoelectric member 160, while being separated from the first electrode layer 140.

The first and second electrode layers 140, 150 may be formed of a highly electrically conductive material by deposition, sputtering, plating, spraying, or the like.

The piezoelectric member 160 is electrically connected to the electrodes 125 of the first connector 120 and the electrodes 135 of the ground connector 130. The piezoelectric member 160 generates ultrasound waves using a resonance phenomenon and may be formed of a ceramic of lead zirconate titanate (PZT), a PZNT single crystal made of a solid solution of lead zinc niobate and lead titanate, a PZMT single crystal made of a solid solution of lead magnesium niobate and lead titanate, or the like.

The piezoelectric member 160 is formed with first and second electrodes 161, 165. The first and second electrodes 161, 165 are disposed on front and rear sides of the piezoelectric member 160, respectively. Here, the first electrode 161 is electrically connected to the first electrode layer 140 and the second electrode 165 is electrically connected to the first electrode layer 150.

The first and second electrodes 161, 165 may be formed of a highly electrically conductive metal. Here, one of the first and second electrodes 161, 165 serves as a positive pole or signal electrode of the piezoelectric member 160, and the other serves as a negative pole or ground electrode of the piezoelectric member 160.

The first and second electrodes 161, 165 are separated from each other to allow the signal electrode and the ground electrode to be separated from each other. In this embodiment, the first and second electrodes 161, 165 are illustrated as serving as the signal and ground electrodes, respectively.

The first and second electrodes 161, 165 are symmetrical to each other such that an upper side of the piezoelectric member 160 is symmetrical to a lower side thereof. Each of the first and second electrodes 161, 165 may have a "J"-shape to surround the piezoelectric member 160. The upper and lower sides of the piezoelectric member 160 including the first and second electrodes 161, 165 are symmetrical to each other, thereby enabling the piezoelectric member 160 to be provided to a probe without being restricted by an orientation, such as the upper or lower side, of the piezoelectric member 160.

According to this embodiment, since the first electrode layer 140 is electrically connected to the electrodes 125 of the first connector 120, the piezoelectric member 160 is electrically connected to the electrodes 125 of the first connector 120 via the first electrode layer 140 and the first electrode 161 which are electrically connected to each other. The first electrode 161 electrically connecting the first electrode layer 140 and the piezoelectric member 160 may be a signal electrode.

Further, since the second electrode layer 150 is electrically connected to the electrodes 135 of the ground connector 130, the piezoelectric member 160 is electrically connected to the electrodes 135 of the ground connector 130 via the second electrode layer 150 and the second electrode 165 which are electrically connected to each other. The second electrode 165 electrically connecting the second electrode layer 150 and the piezoelectric member 160 may be a ground electrode.

The piezoelectric member 160 may be composed of a plurality of piezoelectric members 160 arranged in an array to provide multiple channels. Accordingly, the first electrode layer 140 may also be composed of a plurality of first electrode layers arranged side by side in an array so as to correspond to the piezoelectric members 160 arranged in an array. The piezoelectric members 160 and the first electrode layers 140 are correspondingly connected to the electrodes 125 spaced from each other in the arrangement direction.

According to this embodiment, the probe 100 may further include a sound matching layer 170.

The sound matching layer 170 is disposed on a front side of the piezoelectric member 160. The sound matching layer 170 allows ultrasound signals generated from the piezoelectric member 160 to be efficiently transferred to a target by matching sound impedances of the piezoelectric member 160 and the target. The sound matching layer 170 is configured to have an intermediate value between the sound impedance of the piezoelectric member 160 and the sound impedance of the target.

The sound matching layer 170 may be formed of a glass or resin material, and includes a first sound matching layer 172 and a second sound matching layer 174, which are formed of different materials to allow the sound impedance of the sound matching layer 170 to be changed stepwise from the piezoelectric member 160 to the target.

Although not shown in the drawings, the probe 100 according to this embodiment may further include a lens layer disposed in front of the sound matching layer 170 to focus forwardly traveling ultrasound waves on a predetermined point.

The probe 100 for an ultrasonic diagnostic apparatus according to this embodiment may be a linear type probe having a linear surface or a convex type probe having a convexly rounded surface.

Figure 2:
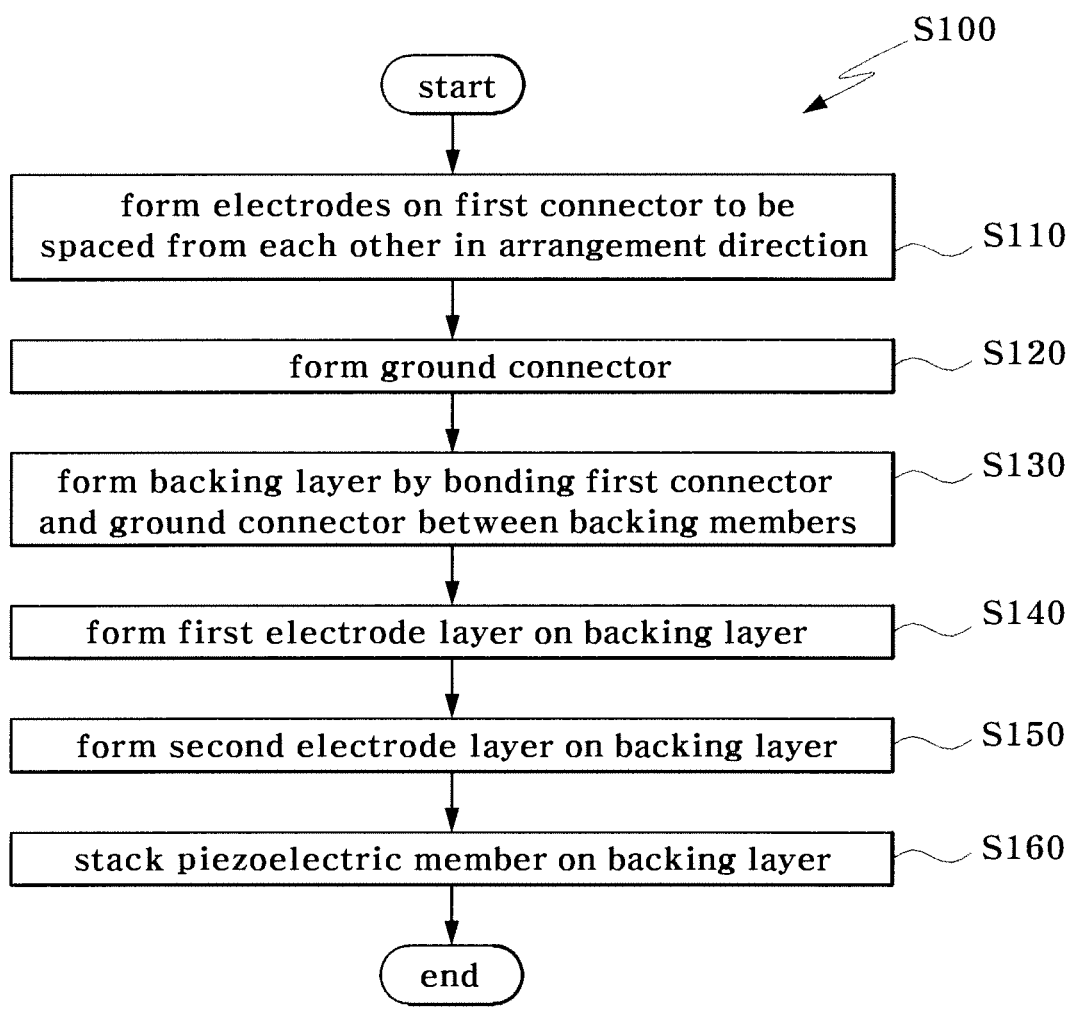
FIG. 2 is a flowchart of a method of manufacturing the probe for an ultrasonic diagnostic apparatus according to the first embodiment of the invention.
Figure 3:
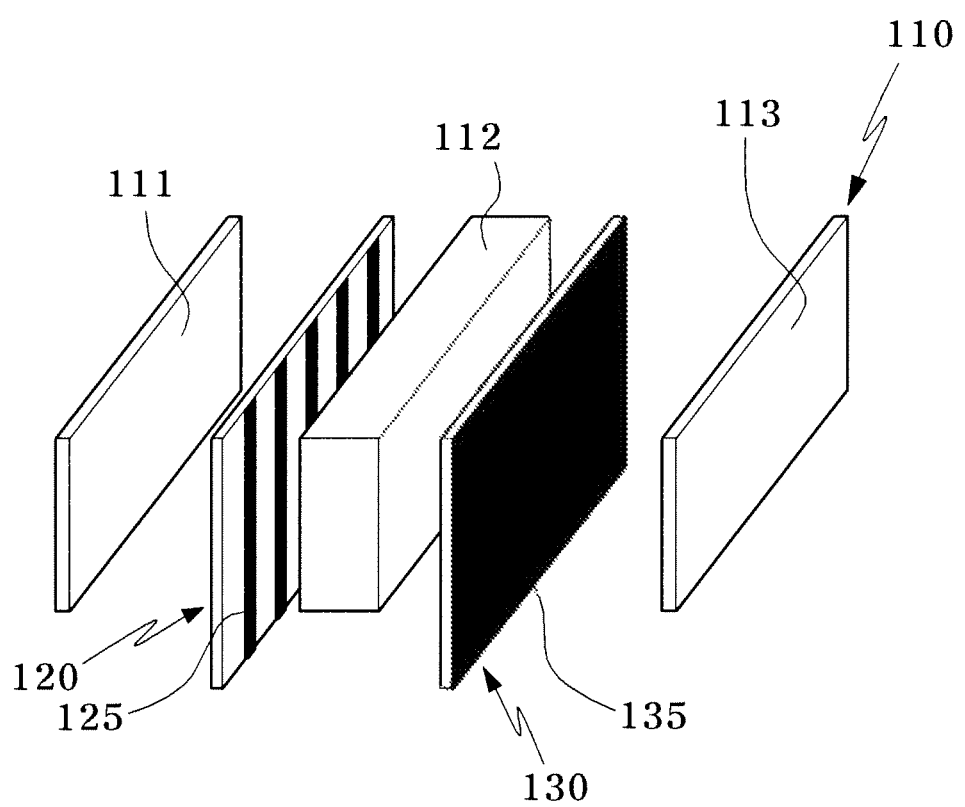
FIGS. 3 and 4 are views of a process of forming a backing layer of the probe according to the first embodiment of the invention.
Figure 4:
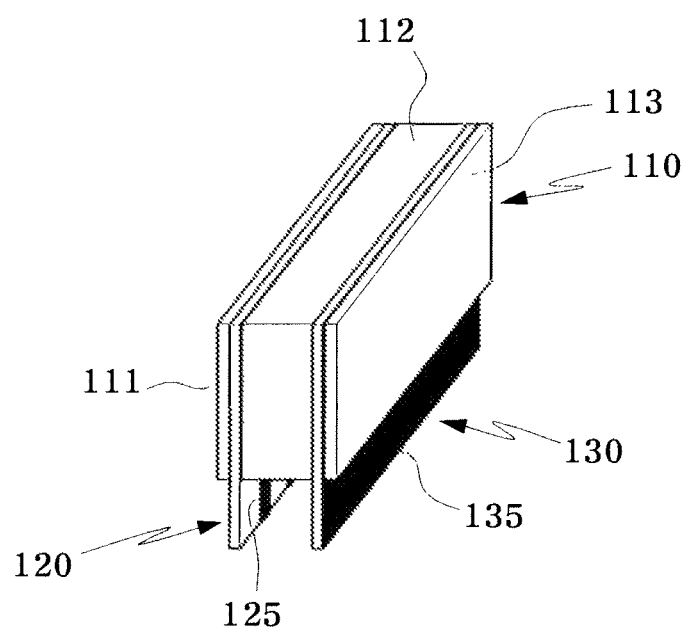
Figure 5:
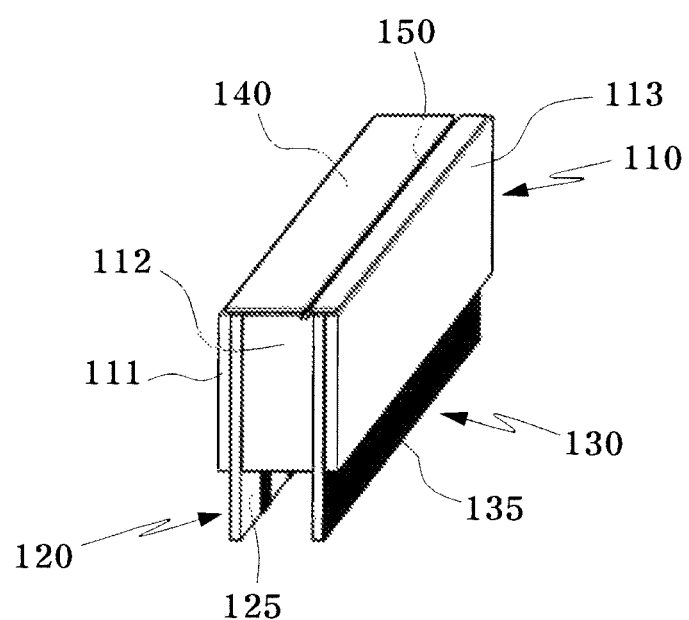
FIG. 5 is a view of a process of forming first and second electrode layers on the backing layer of the probe according to the first embodiment of the invention.

FIG. 2 is a flowchart of a method of manufacturing the probe for an ultrasonic diagnostic apparatus according to the first embodiment of the invention, FIGS. 3 and 4 are views of a process of forming the backing layer of the probe according to the first embodiment of the invention, and FIG. 5 is a view of a process of forming the first and second electrode layers on the backing layer of the probe according to the first embodiment of the invention.

Referring to FIGS. 1 to 5, the method of manufacturing the probe for an ultrasonic diagnostic apparatus according to the first embodiment will now be described.

In the method S100 according to this embodiment, firstly, electrodes 125 are formed on a first connector 120 in S110 and a ground connector 130 is formed in S120, as shown in FIG. 3.

The electrodes 125 of the first connector 120 are formed in the height direction of backing members 111, 112 and are spaced from each other in the arrangement direction in which piezoelectric members 160 are arranged.

In this embodiment, the first connector 120 includes, but is not limited to, a flexible printed circuit board (FPCB). The first connector 120 may include a printed circuit board or any configuration capable of supplying signals or electricity as well as the flexible printed circuit board (FPCB). The ground connector 130 may also include a printed circuit board or any configuration capable of supplying signals or electricity as well as the flexible printed circuit board (FPCB).

Additionally, the ground connector 130 may be formed with electrodes 135, which are the same as or similar to the electrodes 125 of the first connector 120.

While the electrodes 125 are formed on the first connector 120 and the ground connector 130 is formed, the first connector 120 and the ground connector 130 are bonded between backing members 111, 112, 113 to form a backing layer 110 in S130, as shown in FIG. 4.

For this purpose, the backing members 111, 112, 113 are formed of a material including a rubber to which epoxy resin, tungsten powder, and the like are added. Then, with the first connector 120 disposed between the backing members 111, 112 in the height direction, the backing members 111, 112 are bonded to opposite sides of the first connector 120.

Further, with the ground connector 130 disposed between the backing members 112, 113 in the height direction, the backing members 112, 113 are bonded to opposite sides of the ground connector 130, thereby completing formation of the backing layer 110.

One end of each of the first connector 120 and the ground connector 130 bonded between the backing members 111, 112, 113 is exposed on the front side of the backing layer 110 adjacent to the piezoelectric member 160, and the other end thereof extends through the rear side of the backing layer 110.

After the backing layer 110 is formed, a first electrode layer 140 is formed on the backing layer 110 to be electrically connected to the piezoelectric member 160 and the electrodes 125 of the first connector 120 in S140, as shown in FIG. 5.

According to this embodiment, the first electrode layer 140 is formed on a surface of the backing layer 110. Specifically, the first electrode layer 140 may be formed on the front surface of the backing layer 110 adjacent to the piezoelectric member 160.

With this configuration of the first electrode layer 140, the rear side of the first electrode layer 140 adjoining the surface of the backing layer 110 is electrically connected to the electrodes 125 of the first connector 120.

Further, a second electrode layer 150 is formed on the backing layer 110 to be electrically connected to the piezoelectric member 160 and the electrodes 135 of the ground connector 130 in S150.

According to this embodiment, the second electrode layer 150 is formed on a surface of the backing layer 110. Specifically, the second electrode layer 150 may be formed on the front surface of the backing layer 110 adjacent to the piezoelectric member 160 while being separated from the first electrode layer 140.

The first and second electrode layers 140, 150 may be formed of a highly electrically conductive material by deposition, sputtering, plating, spraying, or the like. The first and second electrode layers 140, 150 may be separately formed initially or may be separated from each other by cutting after being integrally formed.

After the first and second electrode layers 140, 150 are formed on the backing layer 110, the piezoelectric member 160 is stacked on the backing layer 110 to be electrically connected to the electrodes 125 of the first connector 120 and the electrodes 135 of the ground connector 130 in S160.

By this process, a first electrode 161 of the piezoelectric member 160 is electrically connected to the first electrode layer 140. As such, since the first electrode layer 140 connected to the first electrode 161 is electrically connected to the electrodes 125 of the first connector 120, the piezoelectric member 160 is electrically connected to the electrodes 125 of the first connector 120 via the first electrode layer 140 and the first electrode 161 which are electrically connected to each other.

Further, a second electrode 165 of the piezoelectric member 160 is electrically connected to the second electrode layer 150. As such, since the second electrode layer 150 connected to the second electrode 165 is electrically connected to the electrodes 135 of the ground connector 130, the piezoelectric member 160 is electrically connected to the electrodes 135 of the ground connector 130 via the second electrode layer 150 and the second electrode 165 which are electrically connected to each other.

According to this embodiment, the piezoelectric member 160 may be divided into multiple piezoelectric members 160 spaced a predetermined distance from each other and arranged side by side in an array, so that the multiple piezoelectric members 160 can be used as multiple channels corresponding to the multiple electrodes 125, 135 formed on the first connector 120 and the ground connector 130, respectively.

Each of the first and second electrode layers 140, 150 may also be divided into multiple electrode layers, which are arranged side by side in an array so as to correspond one-to-one to each of the first and second electrodes 161, 165.

According to this embodiment, stacks of the backing layer 110 and the piezoelectric member 160 are diced by a dicing machine (not shown). Dicing is performed to a depth such that the first and second electrode layers 140, 150 can be reliably divided into the multiple first and second electrode layers, respectively.

By dicing, the piezoelectric member 160 is divided into the multiple piezoelectric members 160 spaced a predetermined distance from each other, such that first and second electrodes 161, 165 formed on each of the piezoelectric members 160 can be electrically completely separated from first and second electrodes 161, 165 formed on other piezoelectric members 160 adjacent thereto.

When the first and second electrode layers 140, 150 are divided into the multiple first and second electrode layers 140, 150 by dicing, each of the divided first electrodes layers 140 and each of the divided second electrode layers 150 are electrically completely separated from other first electrode layers 140 and other second electrode layers 150 adjacent thereto such that only one divided first electrode layer 140 and one divided second electrode layer 150 are connected to the first electrode 161 and the second electrode 165 formed on one divided piezoelectric member 160, respectively.

In this embodiment, the first and second electrode layers 140, 150 are illustrated as being diced together with the piezoelectric member 160 so as to correspond to the first electrode 161 and the second electrode 165 of the piezoelectric member 160. However, the invention is not limited thereto. Alternatively, the first and second electrode layers 140, 150 may be subjected to a patterning process to correspond to the first electrode 161 and the second electrode 165, respectively, by optical etching, etching or the like before the piezoelectric member 160 is stacked on the backing layer 110.

After the piezoelectric member 160 is stacked on the backing layer 110, a sound matching layer 170 is stacked on the piezoelectric member 160 as shown in FIG. 1.

The method S100 of manufacturing a probe for an ultrasonic diagnostic apparatus is not limited to the sequence described above. The processes of the method may be performed in a different sequence or at the same time.

According to this embodiment, in manufacture of the probe 100 for an ultrasonic diagnostic apparatus, the first connector 120 and the ground connector 130 are connected to the piezoelectric member 160 via the first and second electrode layers 140, 150 instead of using a complicated and laborious soldering operation in manufacture of the probe, thereby enabling easy connection between the piezoelectric member 160 and the connectors 120, 130 while preventing deterioration in performance caused by defective connection therebetween and deterioration in performance of the piezoelectric member 160 caused by heat during manufacture.

Further, according to this embodiment, the first connector 120 and the ground connector 130 are bonded between the backing members 111, 112, 113, instead of being disposed between the backing layer 110 and the piezoelectric member 160, to be electrically connected to the piezoelectric member 160 via the first and second electrode layers 140, 150, thereby preventing deterioration in performance caused by defective connection between the piezoelectric member 160, the first connector 120 and the ground connector 130, and preventing damage of the first and ground connectors 120, 130 caused by bending.

Further, according to this embodiment, individual formation and maintenance of the backing layer 110 can be achieved by bonding the first connector 120 and the ground connector 130 to the backing members 111, 112, 113 and forming the first and second electrode layers 140, 150 thereon, so that the backing layer 110 can be prepared in desired shapes and dimensions so as to be easily assembled to other components, thereby enabling easy manufacture of the probe at lower cost while enhancing uniformity of final products.

Further, according to this embodiment, the probe 100 has narrow spaces between the electrodes 125 of the first connector 120, that is, signal electrodes, and the electrodes 135 of the ground connector 130, that is, ground electrodes, thereby reducing noise.

Figure 6:
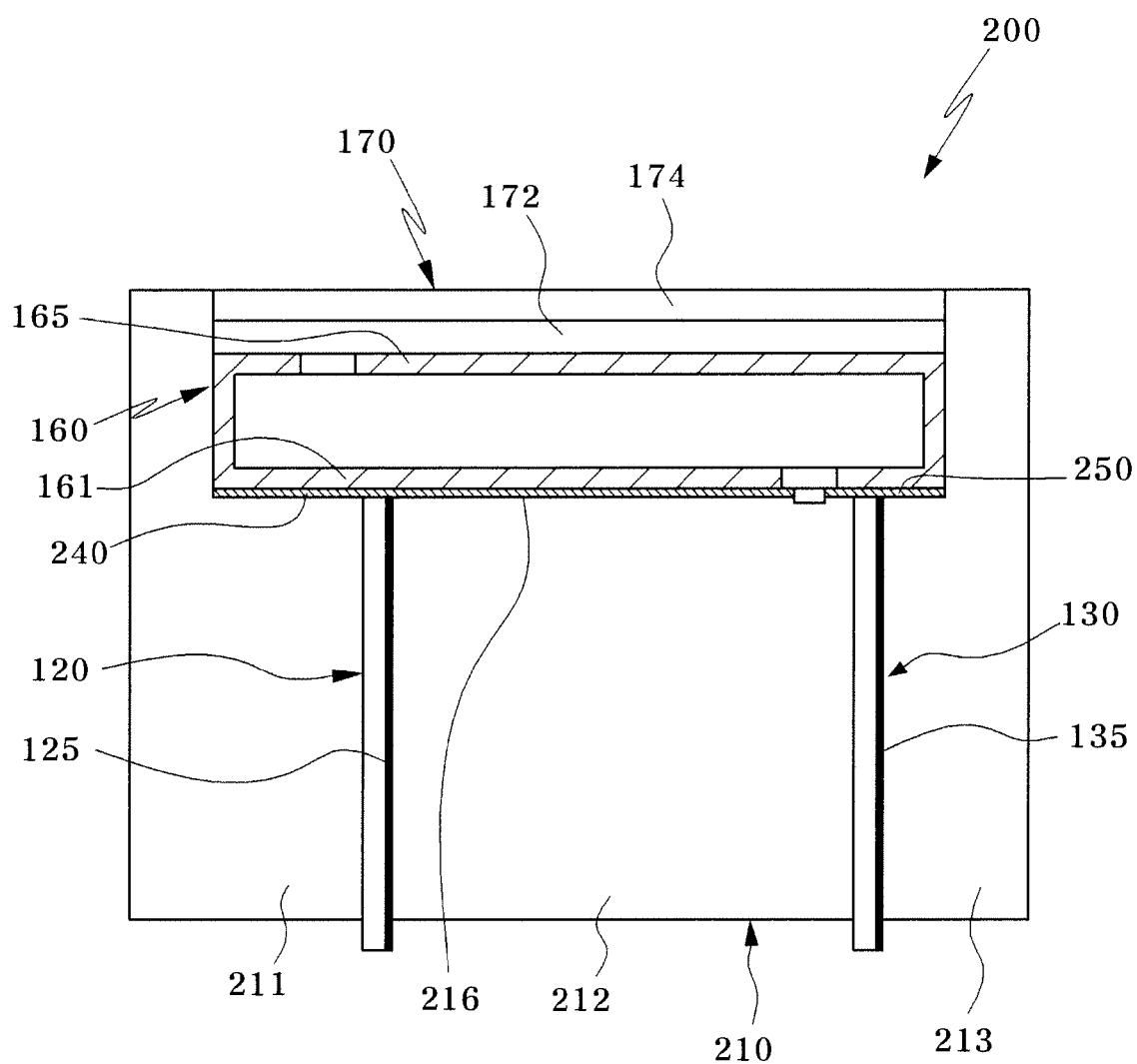
FIG. 6 is a schematic view of a probe for an ultrasonic diagnostic apparatus according to a second embodiment of the invention.

FIG. 6 is a schematic view of a probe for an ultrasonic diagnostic apparatus according to a second embodiment of the invention.

For descriptive convenience, the same or similar components to those of the above embodiment will be denoted by the same reference numerals as those of the above embodiment, and a detailed description thereof will be omitted herein.

Referring to FIG. 6, a probe 200 for an ultrasonic diagnostic apparatus according to the second embodiment includes a backing layer 210.

The backing layer 210 is disposed behind the piezoelectric member 160. The backing layer 210 includes multiple backing members 211, 212, 213 and is formed by bonding the backing members 211, 212, 213. The backing layer 210 may be formed of a material containing a rubber to which epoxy, tungsten powder, and the like are added.

According to this embodiment, a mounting groove 216 is formed on the backing layer 210. The mounting groove 216 is formed on the front side of the backing layer adjacent to the piezoelectric member 160. The piezoelectric member 160 is inserted into the mounting groove 216. The mounting groove 216 is depressed into the backing layer 210 in a shape corresponding to the piezoelectric member 160 to allow the piezoelectric member 160 to be inserted into the backing layer 210.

The backing layer 210 includes first and second electrode layers 240, 250. The first and second electrode layers 240, 250 are formed on the backing layer 210 and are disposed between the backing layer 210 and the piezoelectric member 160. The first and second electrode layers 240, 250 may be formed on the mounting groove 216.

The configuration and operation of the first and second electrode layers 240, 250 are similar to those of the first and second electrode layers 140, 150 according to the first embodiment, and a detailed description thereof will be omitted herein.

Figure 7:
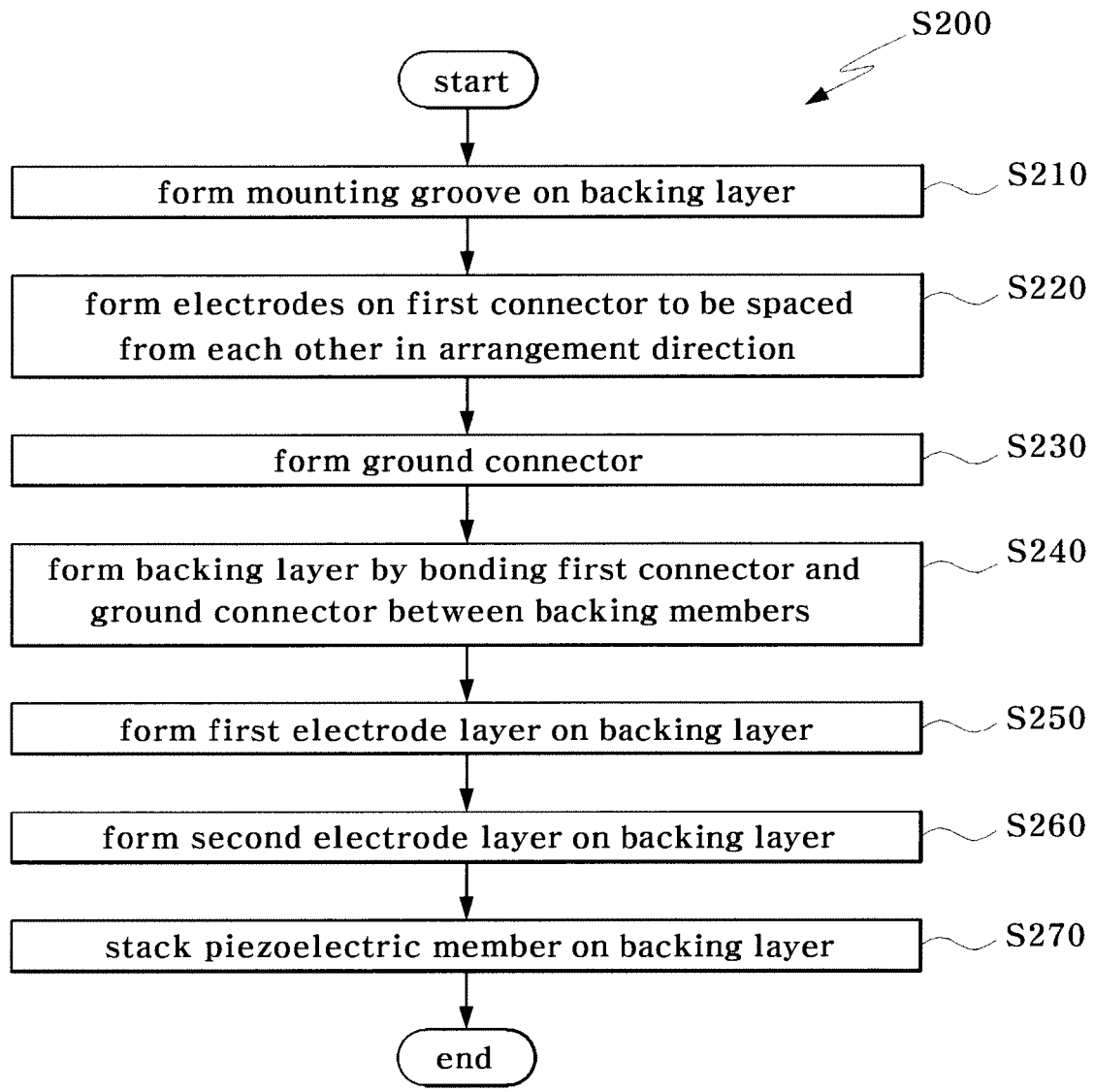
FIG. 7 is a flowchart of a method of manufacturing the probe for an ultrasonic diagnostic apparatus according to the second embodiment of the invention.
Figure 8:
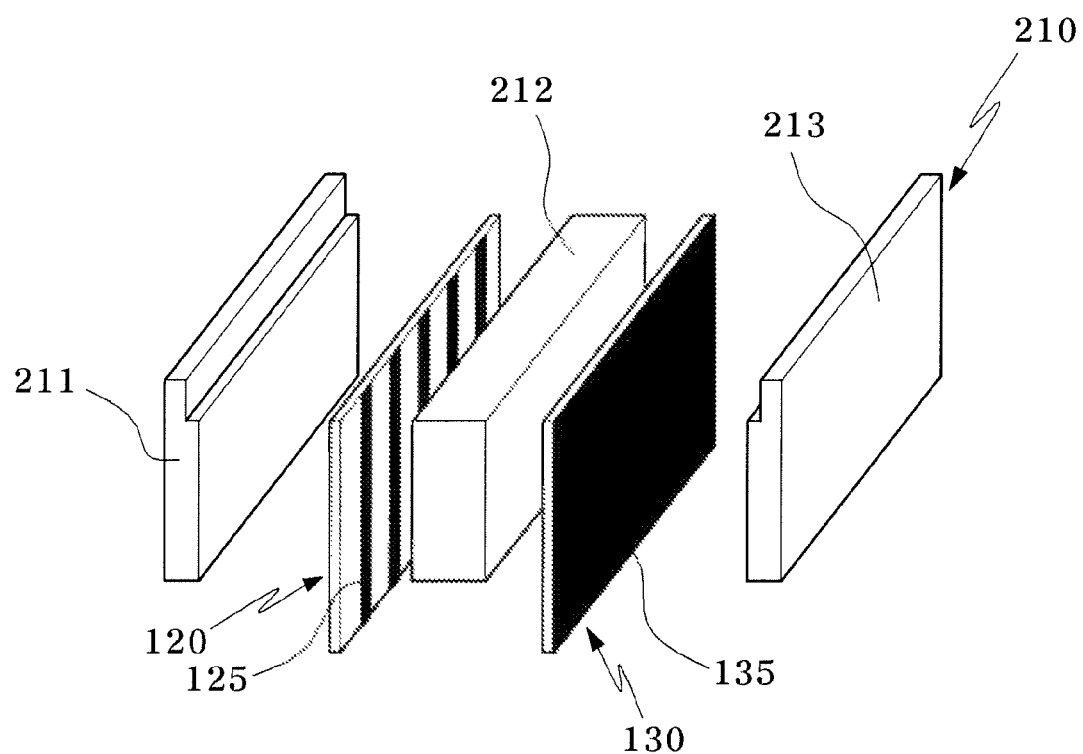
FIGS. 8 and 9 are views of a process of forming a backing layer of the probe according to the second embodiment of the invention.
Figure 9:
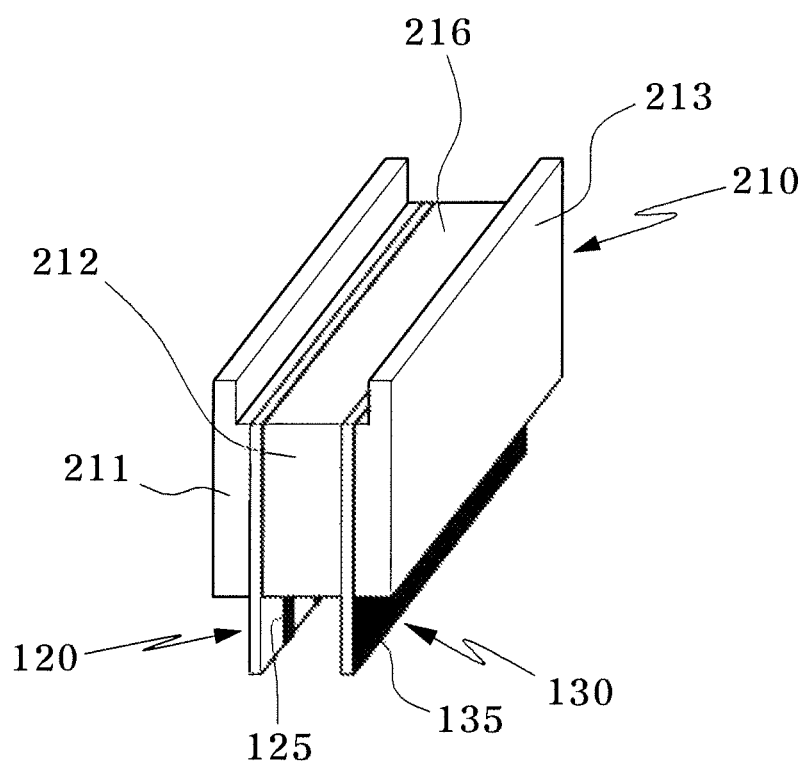
Figure 10:
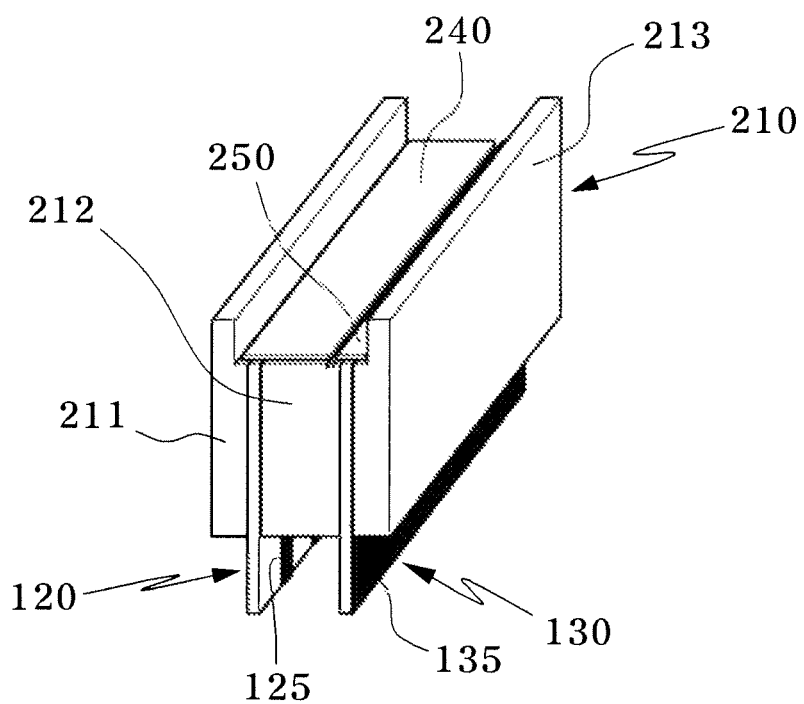
FIG. 10 is a view of a process of forming first and second electrode layers on the backing layer of the probe according to the second embodiment of the invention.

FIG. 7 is a flowchart of a method of manufacturing the probe for an ultrasonic diagnostic apparatus according to the second embodiment of the invention, FIGS. 8 and 9 are views of a process of forming the backing layer of the probe according to the second embodiment of the invention, and FIG. 10 is a view of a process of forming the first and second electrode layers on the backing layer of the probe according to the second embodiment of the invention.

Referring to FIGS. 6 to 10, the method of manufacturing the probe for an ultrasonic diagnostic apparatus according to the second embodiment will now be described.

In the method S200 according to this embodiment, firstly, a mounting groove 216 is formed on a backing layer 210 in S210, as shown in FIG. 8.

For example, in order to form the mounting groove 216 on backing members 211, 212, 213 formed of a material including a rubber to which epoxy resin, tungsten powder, and the like are added, the backing members 211, 213 are formed to have steps at both sides of the backing member 212 interposed between the backing members 211, 213. The backing members 211, 213 are disposed adjacent to the backing layer 212 by forming lower step sections to be coplanar with the backing layer 212 interposed between the backing members 211, 213.

Then, electrodes 125 are formed on a first connector 120 in S220, and a ground connector 130 is formed in S230.

While the electrodes 125 are formed on the first connector 120 and the ground connector 130 is formed as described above, the first connector 120 and the ground connector 130 are bonded between backing members 211, 212, 213 to form a backing layer 210 in S240, as shown in FIG. 9.

After the backing layer 210 is formed, a first electrode layer 240 is formed on the backing layer 210 to be electrically connected to the piezoelectric member 160 and the electrodes 125 of the first connector 120 in S250, as shown in FIG. 10. The first electrode layer 240 may be formed on the mounting groove 216.

With this configuration of the first electrode layer 240, the rear side of the first electrode layer 240 adjoining a surface of the mounting groove 216 is electrically connected to the electrodes 125 of the first connector 120.

Additionally, a second electrode layer 250 is formed on the backing layer 110 to be electrically connected to the piezoelectric member 160 and the electrodes 135 of the ground connector 130 in S260. The second electrode layer 250 may be formed on the mounting groove 216 while being separated from the first electrode layer 240.

With this configuration of the second electrode layer 250, the rear side of the second electrode layer 250 adjoining the surface of the mounting groove 216 is electrically connected to the electrodes 135 of the ground connectors 130.

After the first and second electrode layers 240, 250 are formed on the backing layer 210, the piezoelectric member 160 is stacked on the backing layer 210 by inserting the piezoelectric member 160 into the mounting groove 216 to be electrically connected to the electrodes 125, 135 of the first connector 120 and the ground connector 130 in S270. This configuration is similar to that of the first embodiment, and thus a detailed description thereof will be omitted herein.

After stacking the piezoelectric layer 160 on the backing layer 210 as described above, a sound matching layer 170 is inserted into the mounting groove 216 to stack the sound matching layer 170 on the piezoelectric member 160.

According to this embodiment of the invention, in the probe 200 for an ultrasonic diagnostic apparatus, the mounting groove 216 is formed on the backing members 211, 212, 213 such that the piezoelectric member 160 can be inserted into the mounting groove 216 to thereby reduce the size of the probe and allow easy connection between the piezoelectric member 160 and the first connector 120 and the ground connector 130 while ensuring an enhanced support structure of the piezoelectric member 160 and preventing defective connection and deterioration in performance of the probe caused thereby.

Figure 11:
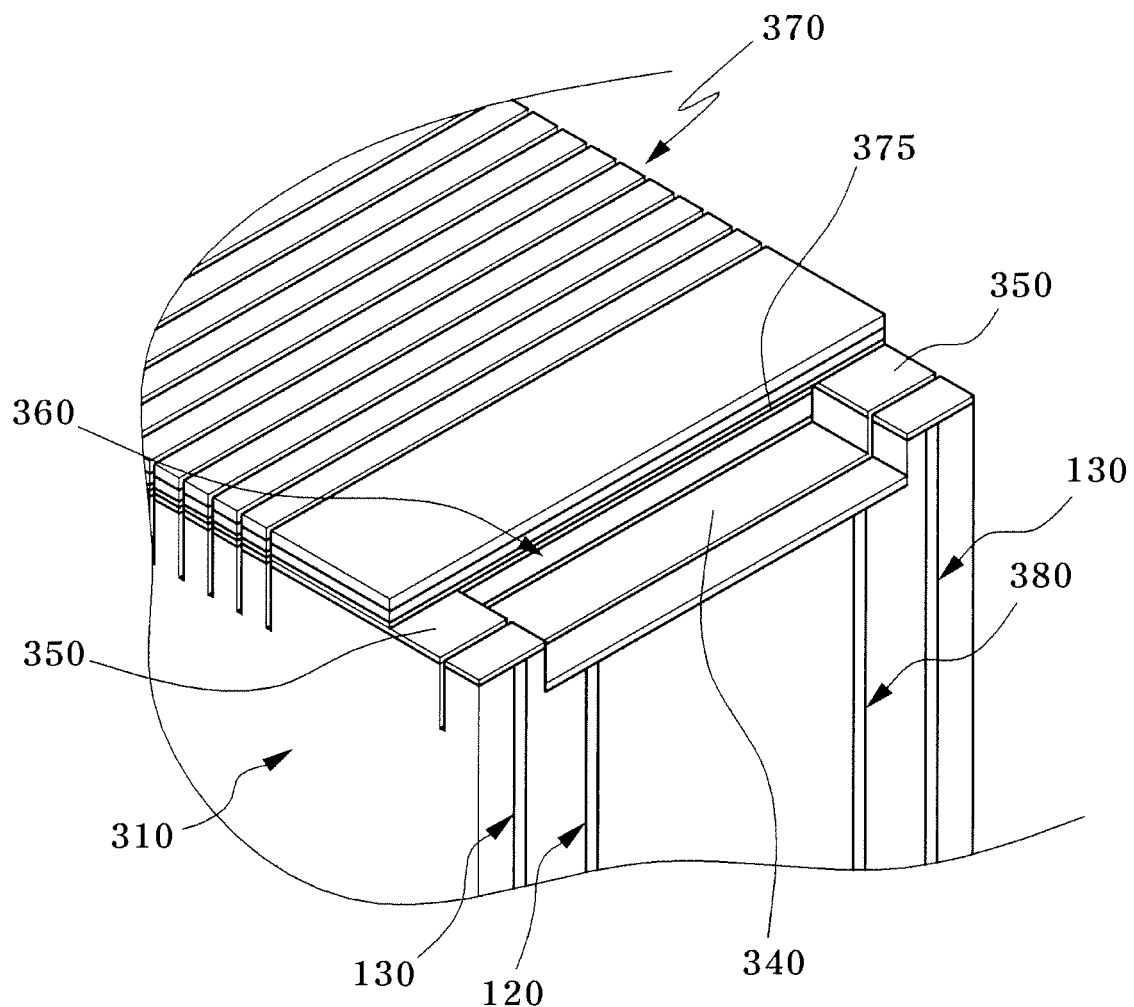
FIG. 11 is a perspective view of a probe for an ultrasonic diagnostic apparatus according to a third embodiment of the invention.
Figure 12:
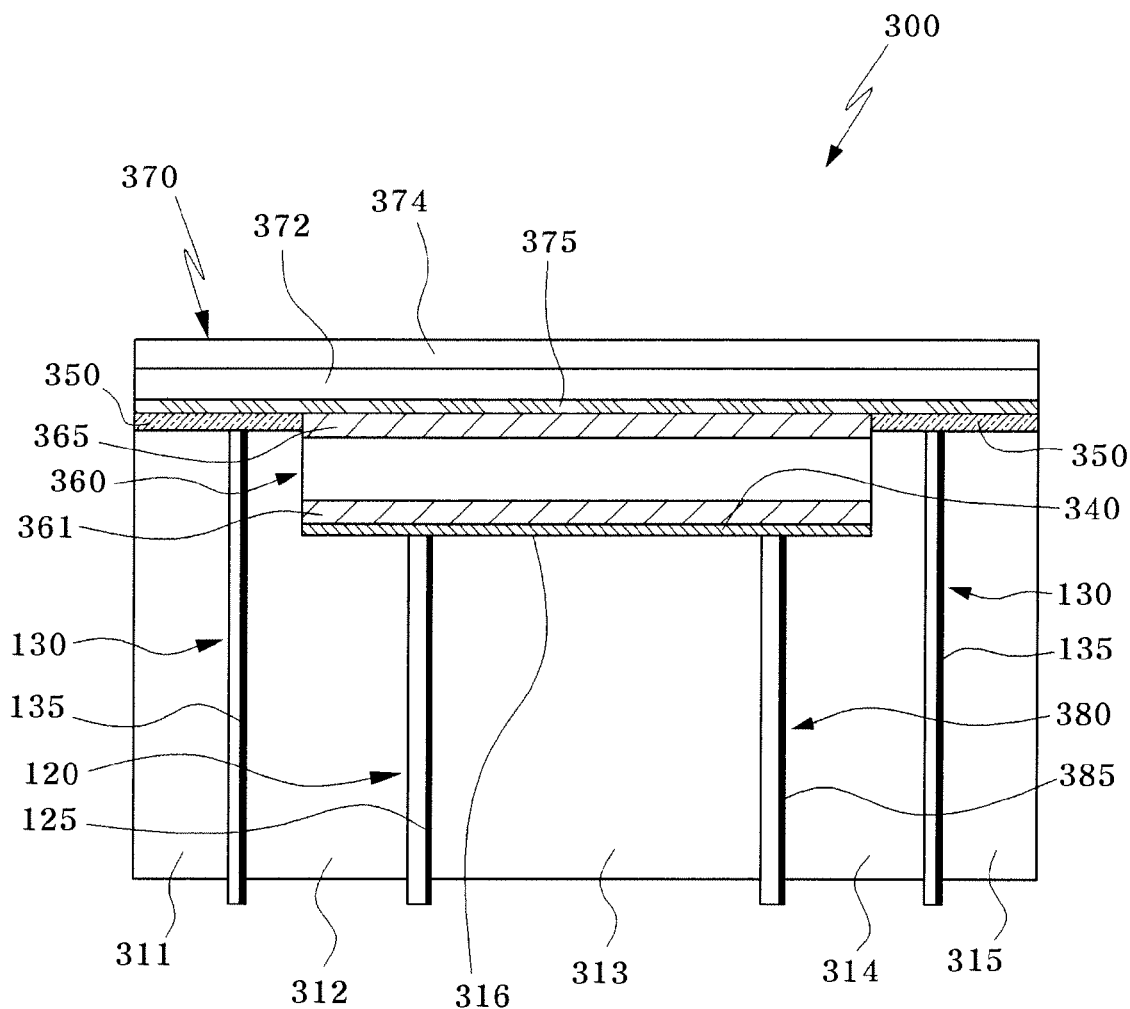
FIG. 12 is a schematic view of the probe shown in FIG. 11.

FIG. 11 is a perspective view of a probe for an ultrasonic diagnostic apparatus according to a third embodiment of the invention, and FIG. 12 is a schematic view of the probe shown in FIG. 11.

For descriptive convenience, the same or similar components to those of the above embodiment will be denoted by the same reference numerals as those of the above embodiment, and a detailed description thereof will be omitted herein.

Referring to FIGS. 11 and 12, a probe 300 for an ultrasonic diagnostic apparatus according to the third embodiment includes a backing layer 310, a first connector 120, a second connector 380, ground connectors 130, a first electrode layer 340, a second electrode layer 350, a piezoelectric member 360, and a sound matching layer 370.

The backing layer 310 is disposed behind the piezoelectric member 360. The backing layer 310 includes multiple backing members 311, 312, 313, 314, 315 and is formed by bonding the backing members 311, 312, 313, 314, 315. The backing layer 310 may be formed of a material containing a rubber to which epoxy, tungsten powder, and the like are added.

A mounting groove 316 is formed on the backing layer 310. The mounting groove 316 is formed on the front side of the backing layer 310 adjacent to the piezoelectric member 360. The piezoelectric member 360 is inserted into the mounting groove 316. The mounting groove 316 is depressed into the backing layer 310 in a shape corresponding to the piezoelectric member 360 to allow the piezoelectric member 360 to be inserted into the backing layer 310.

The first connector 120 is bonded between the backing members 312, 313. According to this embodiment, the first connector 120 is inserted and bonded between two backing members 312, 313 among the five backing members 311, 312, 313, 314, 315.

One end of the first connector 120 bonded between the backing members 312, 313 is exposed on a front side of the backing layer 310 adjacent to the piezoelectric member 360, and the other end thereof extends through a rear side of the backing layer 310. As such, since the one end of the first connector 120 is exposed on the front side of the backing layer 310, electrodes 125 of the first connector 120 are exposed on the front side of the backing layer 310.

The second connector 380 includes an insulation part (reference numeral omitted) and electrodes 385. The multiple electrodes 385 are formed on the insulation part and spaced from each other in the arrangement direction. According to this embodiment, the second connector 380 is inserted and bonded between the backing members 313, 314. The second connector 380 is disposed in the height direction of the backing members 311, 312, 313, 314, 315, and the backing members 313, 314 are bonded to opposite sides of the second connector 380.

One end of the second connector 380 bonded between the backing members 313, 314 is exposed on the front side of the backing layer 310 adjacent to the piezoelectric member 160, and the other end thereof extends through the rear side of the backing layer 310. As such, since the one end of the second connector 380 is exposed on the front side of the backing layer 310, the electrodes 385 of the second connector 380 are exposed on the front side of the backing layer 310.

Like the first connector 120, the second connector 380 may include a flexible printed circuit board (FPCB), a printed circuit board (PCB) or any configuration capable of supplying signals or electricity.

According to this embodiment, the second connector 380 is spaced from the first connector 120 by a width occupied by the backing member 313, and the electrodes 385 of the second connector 380 are disposed to alternate with the electrodes 125 of the first connector 120.

Further, the electrodes 125, 385 of the first and second connectors 120, 380 are signal electrodes that are electrically connected to a first electrode 361 of the piezoelectric member 360.

The ground connectors 130 are bonded between the backing members 311, 312, 314, 315. Each of the ground connectors 130 may comprise multiple ground connectors 130, and the number of ground connectors 130 corresponds to a sum of the number of first connectors 120 and the number of second connectors 380. In this embodiment, two ground connectors 130 are illustrated.

According to this embodiment, one of the ground connectors 130 is disposed adjacent to the first connector 120 and is bonded between the backing members 311, 312. The other ground connector 130 is disposed adjacent to the second connector 380 and is bonded between the backing members 314, 315.

One end of each ground connector 130 bonded between the backing members 311, 312, 314, 315 is exposed on the front side of the backing layer 310 adjacent to the piezoelectric member 360, and the other end thereof extends through the rear side of the backing layer 310. As such, since the one end of the ground connector 130 is exposed on the front side of the backing layer 310, the electrodes 135 of each ground connector 130 are exposed on the front side of the backing layer 310.

Further, the backing layer 310 includes first and second electrode layers 340, 350. The first electrode layer 340 is formed on the mounting groove 316 and the second electrode layer 350 is formed on an upper step section of the backing layer 310 to be spaced from the first electrode layer 340.

According to this embodiment, the first electrode layer 340 is disposed between the mounting groove 316 and the piezoelectric member 360 to be electrically connected to the electrodes 125, 385 of the first and second connectors 120, 380, and the second electrode layer 350 is disposed between an upper step section of the backing layer 310 and a sound matching layer 370 described below to be electrically connected to the electrodes 135 of the ground connectors 130.

The piezoelectric member 360 is electrically connected to the electrodes 125, 385 of the first and second connectors 120, 380 and the electrodes 135 of the ground connectors 130. The piezoelectric member 360 is formed with first and second electrodes 361 and 365. The first and second electrodes 361 and 365 are disposed on front and rear sides of the piezoelectric member 360, respectively. Here, the first electrode 361 is electrically connected to the first electrode layer 340.

The first and second electrodes 361 and 365 may be formed of a highly electrically conductive metal. Here, one of the first and second electrodes 361 and 365 serves as a positive pole or signal electrode of the piezoelectric member 360, and the other serves as a negative pole or ground electrode of the piezoelectric member 360.

The first and second electrodes 361 and 365 are separated from each other to allow the signal electrode and the ground electrode to be separated from each other. In this embodiment, the first and second electrodes 361 and 365 are illustrated as serving as the signal electrode and the ground electrode, respectively.

According to this embodiment, the piezoelectric member 360 is electrically connected to the electrodes 125, 385 of the first and second connectors 120, 380 via the first electrode layer 340 and the first electrode 361 which are electrically connected to each other.

The sound matching layer 370 includes an electrode part 375. The electrode part 375 may be formed of a highly electrically conductive material by deposition, sputtering, plating, spraying, or the like.

The electrode part 375 is electrically connected to a second electrode 365 of the piezoelectric member 360. As a result, the piezoelectric member 360 is electrically connected to the electrode part 375.

In this embodiment, the electrode part 375 is illustrated as being formed on a rear side of a first sound matching layer 372 adjacent to the piezoelectric member 360, but the invention is not limited thereto. According to an alternative embodiment, the sound matching layer 370 may be formed with an electrode part 375 that entirely surrounds the sound matching layer 370. According to another alternative embodiment, the sound matching layer 370 may be entirely or partially (for example, the first sound matching layer) formed of an electrically conductive material so as to be directly electrically connected to the piezoelectric member 360. As such, the sound matching layer can be realized in various forms.

The piezoelectric member 360 may be composed of multiple piezoelectric members 360 arranged in an array to provide multiple channels. Accordingly, each of the first electrode layer 340, the second electrode layer 350, and the electrode part 375 may also be composed of multiple components arranged in an array so as to correspond to the multiple piezoelectric members 360 arranged in an array.

As such, the piezoelectric members 360, first electrode layers 340, second electrode layers 350, and electrode parts 375 arranged in an array are correspondingly connected to the electrodes 125, 385 of the first and second connectors 120, 380 and to the electrodes 135 of the ground connectors 130.

Figure 13:
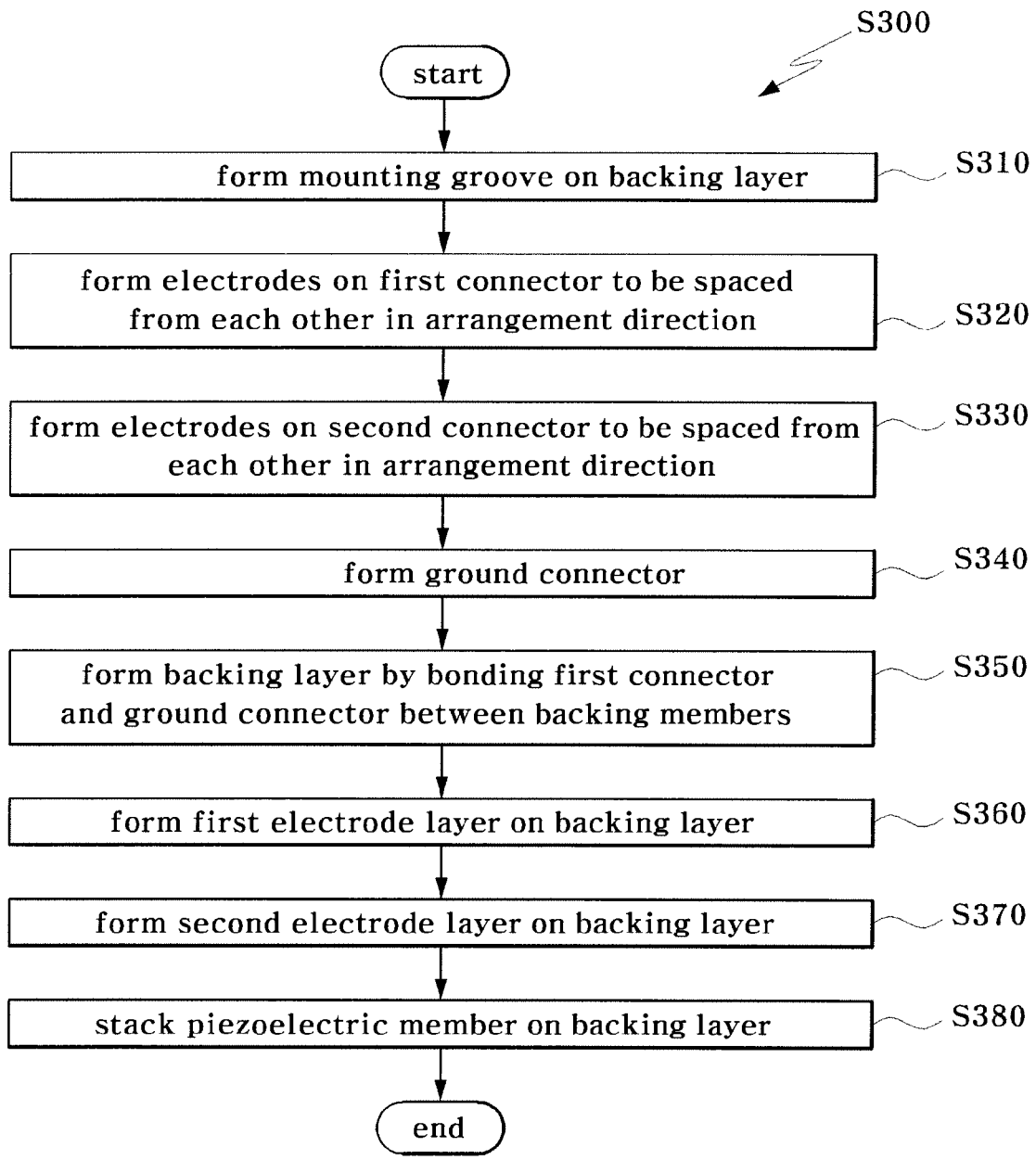
FIG. 13 is a flowchart of a method of manufacturing the probe for an ultrasonic diagnostic apparatus according to the third embodiment of the invention.
Figure 14:
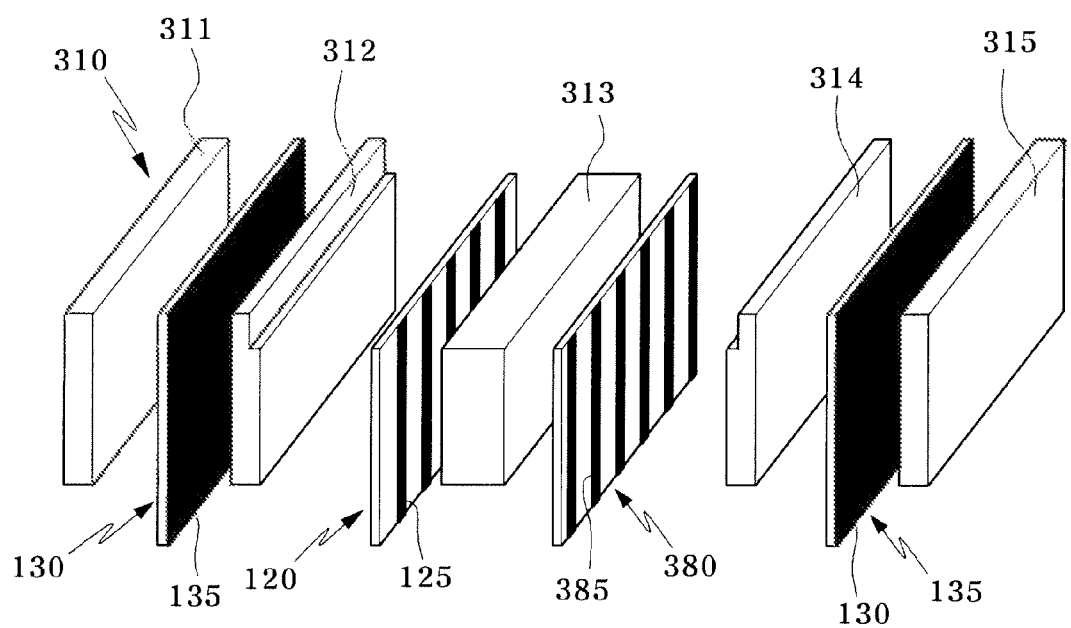
FIGS. 14 and 15 are views of a process of forming a backing layer of the probe according to the third embodiment of the invention.
Figure 15:
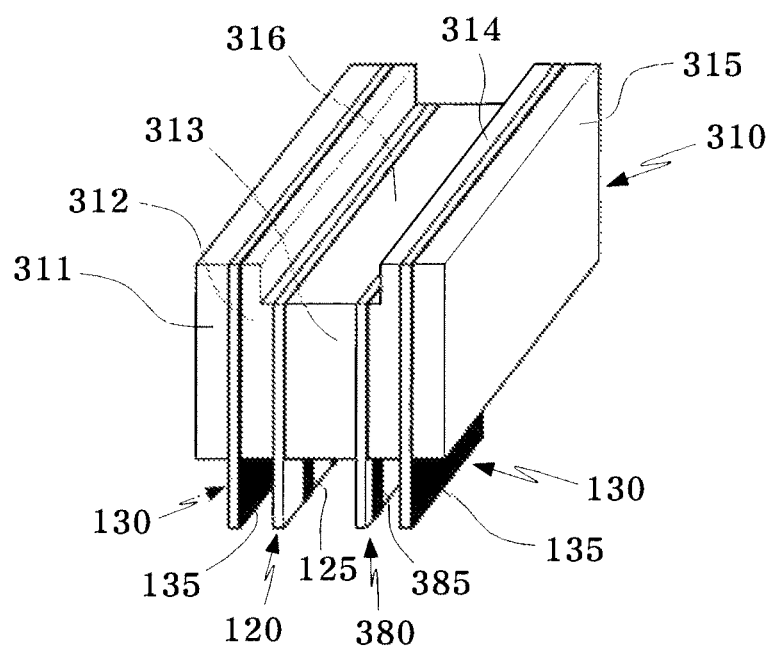
Figure 16:
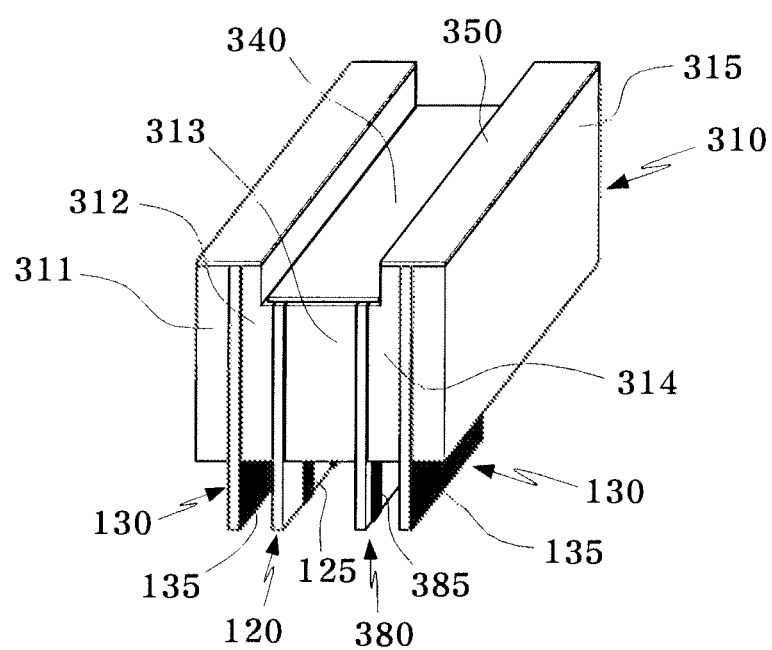
FIG. 16 is a view of a process of forming first and second electrode layers on the backing layer of the probe according to the third embodiment of the invention.

FIG. 13 is a flowchart of a method of manufacturing the probe for an ultrasonic diagnostic apparatus according to the third embodiment of the invention, and FIGS. 14 and 15 are views of a process of forming the backing layer of the probe according to the third embodiment of the invention. Further, FIG. 16 is a view of a process of forming first and second electrode layers on the backing layer of the probe according to the third embodiment of the invention.

Referring to FIGS. 11 to 16, the method of manufacturing the probe for an ultrasonic diagnostic apparatus according to the third embodiment will now be described.

In the method S300 according to this embodiment, firstly, a mounting groove 316 is formed on a backing layer 310, as shown in FIG. 14, in S310.

For example, in order to form the mounting groove 316 on backing members 311, 312, 313, 314, 315 formed of a material including a rubber to which epoxy resin, tungsten powder, and the like are added, the backing members 312, 314 are formed to have steps at both sides of the backing member 313 interposed between the backing members 312, 314.

The backing members 312, 314 are disposed adjacent to the backing layer 313 interposed between the backing members 312, 314 by forming lower step sections to be coplanar with the backing layer 313.

Further, the backing members 311, 315 disposed at opposite sides of the backing members 312, 314 are formed to be coplanar with upper step sections of the backing members 312, 314 which are formed at both sides of the backing member 313 interposed between the backing members 312, 314.

Then, electrodes 125 are formed on a first connector 120 in S320, electrodes 385 are formed on a second connector 380 in S330, and ground connectors 130 are formed in S340.

As such, while the electrodes 125, 385 are respectively formed on the first and second connectors 120, 380 and the ground connectors 130 are formed, the first and second connectors 120, 380 and the ground connectors 130 are bonded between backing members 311, 312, 313, 314, 315 to form a backing layer 310 in S350, as shown in FIG. 15.

For this purpose, the backing members 311, 312, 313, 314, 315 are formed of a material including a rubber to which epoxy resin, tungsten powder, and the like are added. Then, with the ground connectors 130 disposed between the backing members 311, 312 in the height direction, the backing members 311, 312 are bonded to opposite sides of the ground connectors 130.

Further, with the first connector 120 disposed between the backing members 312, 313 in the height direction, the backing members 312, 313 are bonded to opposite sides of the first connector 120, and with the second connector 380 disposed between the backing members 313, 314 in the height direction, the backing members 313, 314 are bonded to opposite sides of the second connector 380.

Additionally, with the ground connectors 130 disposed between the backing members 314, 315 in the height direction, the backing members 314, 315 are bonded to opposite sides of the ground connectors 130, thereby completing formation of the backing layer 310.

One end of each of the first and second connectors 120, 380 and the ground connectors 130 bonded between the backing members 311, 312, 313, 314, 315 is exposed on the front side of the backing layer 310 adjacent to the piezoelectric member 360, and the other end thereof extends through the rear side of the backing layer 310.

Since the one end of the second connector 380 is exposed on the front side of the backing layer 310, the electrodes 385 of the second connector 380 are exposed on the front side of the backing layer 310.

After the backing layer 310 is formed, a first electrode layer 340 is formed on the backing layer 310 to be electrically connected to the piezoelectric member 360 and the electrodes 125, 385 of the first and second connectors 120, 380 in S360, as shown in FIG. 16. The first electrode layer 340 may be formed on the mounting groove 316.

With this configuration of the first electrode layer 340, the rear side of the first electrode layer 340 adjoining the surface of the mounting groove 316 is electrically connected to the electrodes 125 of the first connectors 120.

Additionally, a second electrode layer 350 is formed on the backing layer 310 to be electrically connected to the piezoelectric member 360 and the electrodes 135 of the ground connectors 130 in S370. The second electrode layer 350 may be formed on the mounting groove 316. The second electrode layer 350 is spaced from the first electrode layer 340 and may be formed on an upper step section of the backing layer 310 disposed outside the mounting groove 316.

With this configuration of the second electrode layer 350, the rear side of the second electrode layer 350 adjoining the surface of the upper step section of the backing layer 310 is electrically connected to the electrodes 135 of the ground connectors 130.

After the first and second electrode layers 340, 350 are formed on the backing layer 310, the piezoelectric member 360 is stacked on the backing layer 310 by inserting the piezoelectric member 360 into the mounting groove 316 to be electrically connected to the electrodes 125, 385 of the first and second connectors 120, 380 and to the electrodes 135 of the ground connectors 130 in S380.

By this process, a first electrode 361 of the piezoelectric member 360 is electrically connected to the front side of the first electrode layer 340.

As such, since the first electrode layer 340 connected to the first electrode 361 is electrically connected at the rear side thereof to the electrodes 125, 385 of the first and second connectors 120, 380, the piezoelectric member 360 is electrically connected to the electrodes 125, 385 of the first and second connectors 120, 380 via the first electrode layer 340 and the first electrode 361 which are electrically connected to each other.

According to this embodiment, the piezoelectric member 360 is electrically connected to the electrodes 135 of the ground connectors 130 via the sound matching layer 370.

In other words, after the piezoelectric member 360 is stacked on the backing layer 310, the sound matching layer 370 is stacked on the piezoelectric member 360. By this process, a second electrode 365 of the piezoelectric member 360 is electrically connected to an electrode part 375 of the sound matching layer 370.

As such, since the second electrode part 375 connected to the second electrode 365 is electrically connected to the front side of the second electrode layer 350 and the second electrode layer 350 is electrically connected at the rear side thereof to the electrodes 135 of the ground connectors 130, the piezoelectric member 360 is electrically connected to the electrodes 135 of the ground connectors 130 via the second electrode layer 350, the electrode part 375, and the second electrode 365 which are electrically connected to each other.

According to this embodiment, the piezoelectric member 360 according to this embodiment may be divided into multiple piezoelectric members 360 spaced a predetermined distance from each other and arranged side by side in an array, so that the multiple piezoelectric members 360 can be used as multiple channels corresponding to the multiple electrodes 125, 385, 135 formed on the first, second, and ground connectors 120, 380, 130.

Further, each of the first and second electrode layers 340, 350 and the electrode part 375 is also divided into multiple components so as to correspond to first electrodes 361 and second electrodes 365 of the piezoelectric members 360. The multiple first electrode layers 340, the multiple second electrode layers 350, and the multiple electrode parts 375 may be arranged corresponding to the first and second electrodes 361, 365 of the multiple piezoelectric members 360, respectively.

According to this embodiment, stacks of the backing layer 310 and the piezoelectric member 360 are diced by a dicing machine (not shown). Dicing is performed to a depth such that the first and second electrode layers 340, 350 and the electrode part 375 can be reliably divided into the multiple first and second electrode layers and the multiple electrode parts, respectively.

By dicing, the piezoelectric member 360 is divided into the multiple piezoelectric members 360 spaced a predetermined distance from each other, such that the first and second electrodes 361, 365 formed on each of the piezoelectric members 360 can be electrically completely separated from first and second electrodes 361 and 365 formed on other piezoelectric members 360 adjacent thereto.

When the first electrode layer 340 is divided into the multiple first electrode layers 340 by dicing, each of the first electrodes layers 340 is electrically completely separated from other first electrode layers 340 adjacent thereto such that only one first electrode layer 340 can be connected to a first electrode 361 of one piezoelectric member 360.

Further, when the second electrode layer 350 and the electrode part 375 are divided into the multiple second electrode layers 350 and the multiple electrode parts 375 by dicing, each of the second electrodes layers 350 is electrically completely separated from other second electrode layers 350 adjacent thereto such that a single divided second electrode layer 350 and a single divided electrode part 375 can be connected to a second electrode 365 formed on a single divided piezoelectric member 360.

Figure 17:
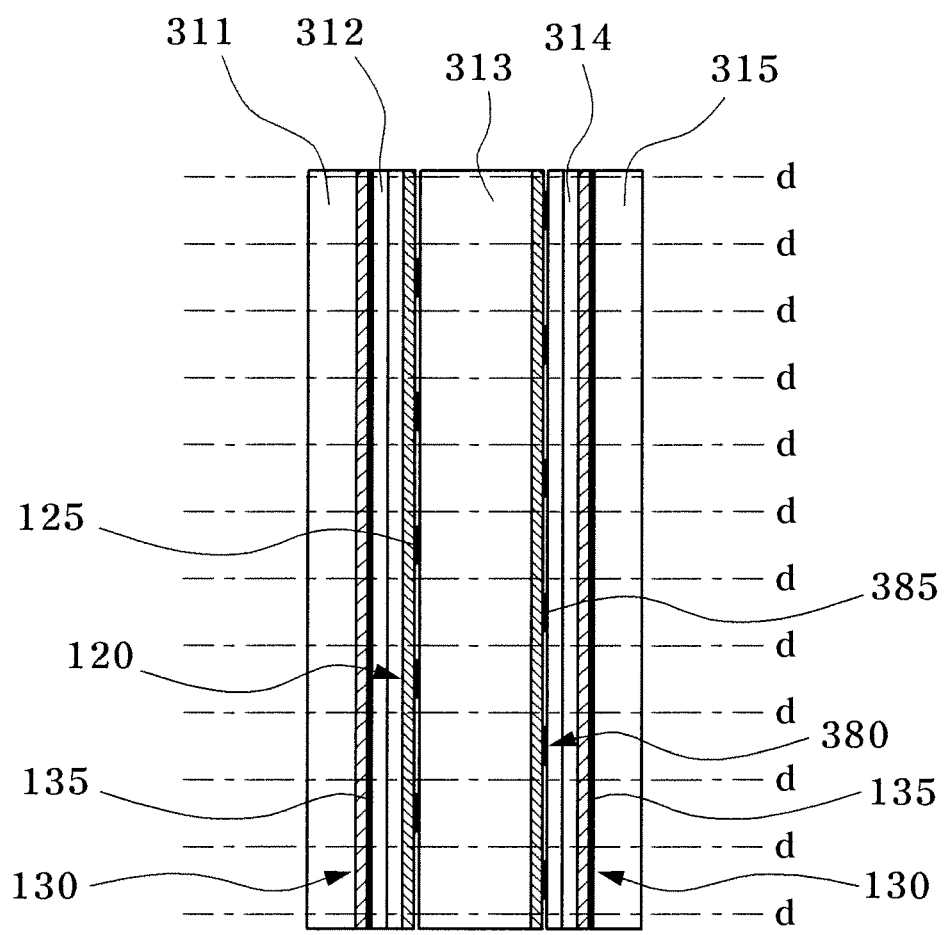
FIG. 17 is a view showing a separated state of the backing layer of the probe according to the third embodiment of the invention.

FIG. 17 is a view showing a separated state of the backing layer of the probe according to the third embodiment of the invention.

Referring to FIG. 17, separation between the backing layer, the first and second connectors and the ground connectors by dicing will be described. In FIG. 17, the first and second electrode layers are omitted.

Referring to FIG. 17, by dicing the stacks of the backing layer 310 and the piezoelectric member 360 (see FIG. 12), the backing layer 310, the first electrode layer 340 (see FIG. 12) formed on the backing layer 310, and the first and second connectors 120 and 380 electrically connected to the first electrode layer 340 are divided as follows.

That is, when the first electrode layer 340 is divided into the multiple first electrode layers 340 by dicing, each of the divided first electrodes layers 340 is electrically completely separated from other first electrode layers 340 adjacent thereto. Here, only one of the electrodes 125, 385 of the first and second connectors 120, 380 is connected to one first electrode layer 340.

For this purpose, when the first electrode layer 340 is divided by dicing, portions of the first connector 120 corresponding to center lines between the respective electrodes 125 of the first connector 120 disposed in the arrangement direction are divided and portions of the second connector 380 corresponding to center lines between the respective electrodes 385 of the second connector 380 disposed in the arrangement direction are divided.

According to this embodiment, since the electrodes 125 of the first connector 120 are disposed to alternate with the electrodes 385 of the second connector 380, the respective dividing lines (d) formed on the first electrode layer 340 to divide the first electrode layer 340 by dicing are formed between the respective electrodes 125 of the first connector 120 and between the respective electrodes 385 of the second connector 380 disposed to alternate with the respective electrodes 125 of the first connector 120.

As a result, only one of the electrodes 125, 385 of the first and second connectors 120, 380 can be connected to one first electrode layer 340.

According to the embodiment, in the probe 300 for an ultrasonic diagnostic apparatus, the piezoelectric member 360 is electrically connected to the first and second connectors 120, 380, that is, multiple connectors 120, 380, so that distances between the first and second connectors 120, 380 and the ground connectors 130 can be decreased.

As a result, the probe 300 according to this embodiment has narrow spaces between the electrodes 125, 385 of the first and second connectors 120, 380, that is, signal electrodes, and the electrodes of the ground connectors 130, that is, ground electrodes, thereby reducing noise.

Further, according to the embodiment, the multiple connectors 120, 130, 380 are bonded in the backing layer 310 and the electrodes 125 of the first connector 120 are disposed to alternate with the electrodes 385 of the second connector 380, so that the respective components of the probe 300 divided by dicing may have sufficient strength and be arranged at a narrower pitch to have a high density and a small size.

As apparent from the description, according to one embodiment of the invention, a first connector and a ground connector or first and second connectors and the ground connector are connected to a piezoelectric member via first and second electrode layers instead of using a complicated and laborious soldering operation in manufacture of the probe, thereby enabling easy connection between the piezoelectric member and the connectors, preventing deterioration in performance caused by defective connection therebetween, and preventing deterioration in performance of the piezoelectric member caused by heat during manufacture.

Further, according to one embodiment of the invention, the first connector and the ground connector or the first and second connectors and the ground connector are bonded between backing members, instead of being disposed between a backing layer and the piezoelectric member, to be electrically connected to the piezoelectric member via the first and second electrode layers, thereby preventing deterioration in performance caused by defective connection between the piezoelectric member, the first connector and the ground connector or between the piezoelectric member, the first and second connectors and the ground connector, and preventing damage of the first and second connectors and the ground connector caused by bending.

Further, according to one embodiment of the invention, individual formation and maintenance of the backing layer can be achieved by bonding the first connector and the ground connector or the first and second connectors and the ground connector to the backing members and forming the first and second electrode layers thereon, so that the backing layer can be prepared in desired shapes and dimensions so as to be easily assembled to other components, thereby enabling easy manufacture of the probe at lower cost while enhancing uniformity of final products.

Further, according to one embodiment of the invention, the probe has narrow spaces between signal electrodes and ground electrodes, thereby reducing noise.

Further, according to one embodiment of the invention, the piezoelectric member is inserted into a mounting groove formed on the backing layer, thereby enabling size reduction and easy connection between the piezoelectric member, the first connector and the ground connector or between the piezoelectric member, the first and second connectors, and the ground connector while providing a more rigid support structure to the piezoelectric member to prevent deterioration in performance caused by defective connection therebetween.

Further, according to one embodiment of the invention, electrodes of the first connector alternate with those of the second connector, so that respective components divided by dicing have sufficient strength at a narrower pitch to have a high density and a small size.

In understanding the scope of the invention, the terms "part" or "member" when used in the singular can have the dual meaning of a singular part or a plurality of parts unless otherwise stated. Further, the use of articles "a," "an" and "the" in the context of describing the invention, especially in the context of the embodiments, are to be construed to cover both the singular and the plural unless otherwise indicated herein or clearly contradicted by context Although some embodiments have been provided to illustrate the invention in conjunction with the drawings, it will be apparent to those skilled in the art that the embodiments are given by way of illustration only, and that various modifications and equivalent embodiments can be made without departing from the spirit and scope of the invention. Accordingly, the scope of the invention should be limited only by the accompanying claims.

What is claimed is:

1. A probe for an ultrasonic diagnostic apparatus, comprising:
    a backing layer including backing members;
    a first connector bonded between the backing members and including first connector electrodes spaced from each other;
    a second connector bonded between the backing members to be spaced from the first connector and including second connector electrodes spaced from each other;

a ground connector bonded between the backing members to be spaced from the first connector and second connector;

a piezoelectric member electrically connected to the first connector electrodes, the second connector electrodes and the ground connector, wherein:

the second connector is disposed such that the first connector electrodes alternate with the second connector electrodes, and the first connector electrodes are electrically separated from the second connector electrodes.

2. The probe according to claim 1, wherein the first connector and the ground connector comprise a flexible printed circuit board (FPCB).

3. The probe according to claim 1, wherein the backing layer comprises a first electrode layer electrically connected to the first connector electrodes and the second connector electrodes.

4. The probe according to claim 3, wherein the first electrode layer is disposed on a surface of the backing layer.

5. The probe according to claim 3, wherein the backing layer further comprises a second electrode layer electrically connected to the ground connector.

6. The probe according to claim 5, wherein the second electrode layer is disposed on a surface of the backing layer, and separated from the first electrode layer.

7. The probe according to claim 5, wherein:

the second electrode layer is disposed on an upper step of the backing layer, and the first electrode layer is disposed on a lower step of the backing layer.

8. The probe according to claim 1, wherein the backing layer has a mounting groove and the piezoelectric member is disposed in the mounting groove.

9. The probe according to claim 1, wherein the first connector electrodes and the second connector electrodes are signal electrodes.

10. A method of manufacturing a probe for an ultrasonic diagnostic apparatus, characterized by comprising:

forming first connector electrodes spaced from each other on a first connector;

forming second connector electrodes spaced from each other on a second connector;

forming a ground connector;

forming a backing layer by bonding the ground connector, the first connector and the second connector between backing members; and stacking a piezoelectric member on the backing layer such that the piezoelectric member is electrically connected to the ground connector, the first connector electrodes and the second connector electrodes, wherein:

the forming a backing layer comprises disposing the second connector such that the first connector electrodes alternate with the second connector electrodes, and the first connector electrodes are electrically separated from the second connector electrodes.

11. The method according to claim 10, further comprising:

after forming the backing layer, forming a first electrode layer on the backing layer such that the first electrode layer is electrically connected to the piezoelectric member, the first connector electrodes and the second connector electrodes.

12. The method according to claim 10, further comprising:

after forming the backing layer, forming a second electrode layer on the backing layer such that the second electrode layer is electrically connected to the piezoelectric member and the ground connector.

13. The method according to claim 12 wherein the second electrode layer is separate from the first electrode layer.

14. The method according to claim 10, further comprising:

forming a mounting groove on the backing layer, wherein the stacking a piezoelectric member on the backing layer comprises inserting the piezoelectric member into the mounting groove.

* * * * *